US012653545B2

(12) United States Patent
Beverland et al.

(10) Patent No.: US 12,653,545 B2
(45) Date of Patent: Jun. 16, 2026

(54) FEMORAL NECK RESECTION JIG

(71) Applicant: DEPUY IRELAND UNLIMITED COMPANY, Ringaskiddy (IE)

(72) Inventors: David Beverland, Holywood (GB); Sarah Radcliffe, Manchester (GB); Jason Naylor, Leeds (GB)

(73) Assignee: DEPUY IRELAND UNLIMITED COMPANY, LOUGHBEG INDUSTRIAL ESTATE, Ringaskiddy (IE)

( * ) Notice: Subject to any disclaimer, the term of this patent is extended or adjusted under 35 U.S.C. 154(b) by 98 days.

(21) Appl. No.: 18/675,707

(22) Filed: May 28, 2024

(65) Prior Publication Data

US 2024/0341771 A1 Oct. 17, 2024

Related U.S. Application Data

(63) Continuation of application No. 17/251,938, filed as application No. PCT/EP2019/066596 on Jun. 24, 2019, now Pat. No. 11,992,226.

(30) Foreign Application Priority Data

Jun. 26, 2018 (GB) ...................................... 1810479
Mar. 27, 2019 (GB) ...................................... 1904244

(51) Int. Cl.
A61B 17/15 (2006.01)
A61B 90/00 (2016.01)

(52) U.S. Cl.
CPC .............. *A61B 17/15* (2013.01); *A61B 90/08* (2016.02); *A61B 2090/0811* (2016.02)

(58) Field of Classification Search
CPC ................................ A61B 17/15; A61B 17/17
See application file for complete search history.

(56) References Cited

U.S. PATENT DOCUMENTS 4,335,715 A 6/1982 Kirkley
4,621,630 A 11/1986 Kenna
(Continued)

FOREIGN PATENT DOCUMENTS

AU 2006200152 A1 8/2006
CN 107149490 A 9/2017
(Continued)

OTHER PUBLICATIONS

International Search Report and Written Opinion, received for PCT Application No. PCT/EP2019/060894, mailed on Aug. 9, 2019, 17 pages.
(Continued)

*Primary Examiner* — Christian A Sevilla

(57) ABSTRACT

The invention provides a surgical apparatus for performing a controlled resection of the neck of a femur during a hip replacement procedure, the surgical apparatus comprising: a body portion. The body portion comprises a frame that is mountable on a femoral head of the femur to position the body portion with respect to a centre of the femoral head. The body portion also includes a resection guide for indicating a position of a resection plane on the femoral neck, and an arm extending from the frame and including markings for reading off a femoral head offset. The apparatus also includes a connector for mounting the body portion on an intramedullary rod located in an intramedullary canal of the femur, and for slidably receiving the arm. The connector includes a pointer. The femoral head offset is indicated by reading the position of the pointer relative to the markings on the arm.

7 Claims, 12 Drawing Sheets

(56) References Cited

U.S. PATENT DOCUMENTS

| | | | |
|---|---|---|---|
| 4,959,066 A | 9/1990 | Dunn et al. | |
| 5,464,406 A | 11/1995 | Ritter et al. | |
| 5,578,037 A | 11/1996 | Sanders et al. | |
| 5,607,431 A | 3/1997 | Dudasik et al. | |
| 5,662,656 A * | 9/1997 | White | A61B 17/155 |
| | | | 606/88 |
| 6,258,097 B1 | 7/2001 | Cook et al. | |
| 6,421,630 B1 | 7/2002 | Yamada et al. | |
| 6,503,255 B1 | 1/2003 | Albrektsson et al. | |
| 7,582,091 B2 | 9/2009 | Duncan et al. | |
| 7,601,155 B2 | 10/2009 | Petersen | |
| 7,833,275 B2 | 11/2010 | Mears et al. | |
| 8,246,621 B2 | 8/2012 | Poncet | |
| 8,821,499 B2 | 9/2014 | Iannotti et al. | |
| 8,939,982 B2 | 1/2015 | Chellaoui | |
| 10,226,262 B2 | 3/2019 | Kehres et al. | |
| 10,568,647 B2 | 2/2020 | Kehres et al. | |
| 10,668,559 B2 | 6/2020 | Hori et al. | |
| 10,980,646 B2 | 4/2021 | Grobler et al. | |
| 11,992,226 B2 * | 5/2024 | Beverland | A61B 17/15 |
| 2001/0053935 A1 | 12/2001 | Hartdegen et al. | |
| 2002/0165552 A1 | 11/2002 | Duffner | |
| 2003/0009170 A1 | 1/2003 | Tornier | |
| 2004/0122439 A1 | 6/2004 | Dwyer et al. | |
| 2004/0236341 A1 * | 11/2004 | Petersen | A61B 17/15 |
| | | | 606/88 |
| 2005/0245934 A1 | 11/2005 | Tuke et al. | |
| 2005/0245936 A1 | 11/2005 | Tuke et al. | |
| 2007/0162039 A1 | 7/2007 | Wozencroft | |
| 2008/0103506 A1 * | 5/2008 | Volpi | A61B 17/1764 |
| | | | 606/96 |
| 2009/0222010 A1 | 9/2009 | Lafosse et al. | |
| 2012/0022543 A1 | 1/2012 | Porzel et al. | |
| 2012/0130382 A1 | 5/2012 | Lannotti et al. | |
| 2014/0276866 A1 | 9/2014 | Endsley et al. | |
| 2015/0320430 A1 | 11/2015 | Kehres et al. | |
| 2018/0243858 A1 | 8/2018 | Hori et al. | |
| 2021/0219995 A1 * | 7/2021 | Nelson | A61B 17/1735 |
| 2021/0236145 A1 | 8/2021 | Beverland | |
| 2021/0259705 A1 | 8/2021 | Beverland et al. | |
| 2021/0259706 A1 | 8/2021 | Atkin et al. | |
| 2021/0259707 A1 | 8/2021 | Beverland et al. | |
| 2022/0370083 A1 * | 11/2022 | Alspaugh | A61B 17/15 |
| 2025/0134536 A1 * | 5/2025 | Seo | A61B 34/10 |

FOREIGN PATENT DOCUMENTS

| | | |
|---|---|---|
| CN | 107981866 A | 5/2018 |
| EP | 1797834 A1 | 6/2007 |
| JP | 2008188400 A | 8/2008 |
| TW | 201540251 A | 11/2015 |
| WO | 0226145 A1 | 4/2002 |
| WO | 03009170 A1 | 1/2003 |
| WO | 2005110250 A1 | 11/2005 |
| WO | 2014125253 A1 | 8/2014 |
| WO | 2020001830 A1 | 1/2020 |
| WO | 2020001832 A1 | 1/2020 |
| WO | 2020002190 A1 | 1/2020 |
| WO | 2020002198 A1 | 1/2020 |

OTHER PUBLICATIONS

International Search Report and Written Opinion, received for PCT Application No. PCT/EP2019/060976, mailed on Aug. 7, 2019, 17 pages.

International Search Report and Written Opinion, received for PCT Application No. PCT/EP2019/066596, mailed on Oct. 7, 2019, 13 pages.

International Search Report and Written Opinion, received for PCT Application No. PCT/EP2019/066612, mailed on Oct. 1, 2019, 15 pages.

Great Britain Search report, received for GB Application No. 1810475.2, mailed on Dec. 21, 2018, 4 pages.

Great Britain Search report, received for GB Application No. 1810477.8, mailed on Dec. 20, 2018, 1 page.

Hangbo et al., "Bipolar Hemiarthroplasty Clinical Analysis of 101 Cases of Femoral Neck Subcapital Fracture Treated with Replacement", Chinese Journal of Disability Medicine, vol. 21, No. 2, pp. 37-39, Dec. 31, 2013.

* cited by examiner

FEMORAL NECK RESECTION JIG

CROSS-REFERENCE TO RELATED APPLICATIONS

This application is a continuation application of Ser. No. 17/251,938, entitled "Femoral Neck Resection Jig" and filed Jun. 24, 2019, which was a national stage entry under 35 U.S.C. § 371(b) of PCT International Application No. PCT/EP2019/066596, entitled "Femoral Neck Resection Jig" and filed Jun. 24, 2019, which claims priority to Great Britain Patent Application No. 1904244.9, filed on Mar. 27, 2019 and to Great Britain Patent Application No. 1810479.4, filed on Jun. 26, 2018, the entire disclosures of which are expressly incorporated herein by reference.

FIELD OF THE INVENTION

This invention relates to a surgical device and method for performing a controlled resection of the neck of a femur during a hip replacement procedure.

BACKGROUND OF THE INVENTION

Hip replacement is a surgical procedure in which the hip joint is replaced by a prosthetic implant. In total hip replacement surgery, a patient's natural hip is replaced by an acetabular cup component that replaces the acetabular socket and a femoral component that replaces the femoral head.

During such a surgical procedure, a discased portion of the femur is excised, usually by resecting along a portion of the femoral neck. A prosthetic femoral component and a prosthetic femoral head replace the natural structures that are surgically removed. The positioning of the femoral component of the prosthesis is important to ensure proper fit and smooth rotation of the femoral head within its socket (i.e., the acetabular shell).

When performing joint reconstruction, such as hip replacement surgery, it is important that the pre-surgical geometry of the bone structure is replicated in the post-surgical structure. It is important to maintain the natural joint biomechanics, ensuring proper joint and soft tissue balancing. If this is not achieved, the result can be higher joint forces, and overall joint instability.

It is therefore necessary to ensure that orthopedic implant structures are properly placed within a patient. In the case of hip joint prostheses, it is important that the native anatomic centre of rotation of the femoral head within the acetabular shell be located and maintained during the implantation of the replacement structure. Misplacement of the centre of rotation during implantation of the femoral component of the hip joint prosthesis can affect the patient's leg length can lead to a very unsatisfactory result for the patient.

It is important in primary total hip arthroplasty to determine the natural offset and neck length of the femoral head by measurement. Offset can be measured from a point on the greater trochanter to the centre of the femoral head. Neck length can be measured from a point of the lesser trochanter to the centre of the femoral head.

U.S. Pat. No. 6,258,097 discloses an orthopaedic instrument for comparing post-surgical joint geometry to pre-surgical joint geometry. The instrument includes a head chuck that can be secured to the ball of a ball joint, and an arm having reference indicia thereon. Markings indicative of the pre-surgical joint geometry are made on the bone with reference to the centre of the ball joint. After replacement with a prosthetic ball, the post-operative geometry is verified by securing the head chuck to the prosthetic ball, and comparing the location of the bone markings against the reference indicia on the arm. As needed, adjustments are made in the prosthetic components.

Image based systems are also widely used within hip arthroplasty to locate the femoral head centre. There systems require pre-operative imaging and intra-operative verification.

There remains a need for surgical instruments that will assist a surgeon to measure the femoral head offset, without the need for error-prone complex mathematical calculations to be performed during surgery. There also remains a need for surgical instruments to assist a surgeon in resecting the femoral neck at the appropriate resection plane in order to reproduce within the artificial joint the hip's anatomic centre of rotation.

SUMMARY OF THE INVENTION

Aspects of the invention are set out in the accompanying independent and dependent claims. Combinations of features from the dependent claims may be combined with features of the independent claims as appropriate and not merely as explicitly set out in the claims.

There is provided a surgical apparatus for performing a controlled resection of the neck of a femur during a hip replacement procedure, the surgical apparatus comprising:
    a body portion comprising:
        a frame comprising an aperture, wherein the aperture is dimensioned for receiving a femoral head of the femur to position the body portion with respect to a centre of the femoral head;
        a resection guide for indicating a position of a resection plane on the femoral neck, and
        an arm extending from the frame and including markings for reading off a femoral head offset,
    a connector for mounting the body portion on an intramedullary rod located in an intramedullary canal of the femur, and for slidably receiving the arm and wherein the connector includes a pointer, the femoral head offset being indicated by reading the position of the pointer relative to the markings on the arm.

The surgical apparatus according to the invention is a femoral neck resection jig. The apparatus is a "reality based" rather than an "image based" system for determining the femoral head centre. This is because apparatus uses the actual in situ femoral head to locate the femoral head centre, prior to its resection. As such, the surgical apparatus as described herein provides at least a quicker, cheaper, easier to use, and more accurate means of locating this key anatomical parameter, than conventional "image based" systems.

The concept is based around finding the femoral head centre and then making a neck resection in relation to that femoral head centre.

The Frame

The frame is a simple ring structure dimensioned to be removably mountable onto the femoral head. The aperture of the frame positions the body portion of the apparatus with respect to a centre of the femoral head. The frame may be referred to by those skilled in the art as a "spherometer". It has been demonstrated that the posterior aspect of the femoral head can be used to determine femoral head centre even during the late stages of osteoarthritis, as it seems to maintain its sphericity more so in comparison to the anterior aspect. However, use of the surgical apparatus is not limited to the mounting of the frame on the posterior aspect of the femoral head, and it is also envisaged that the frame may be mounted on the anterior aspect of the femoral head.

The frame may include a pin hole configured for removable receipt of a bone pin for removably mounting the frame on the femoral head.

The pin holes may be angled such that the pin hole points towards the centre of the femoral head (i.e., the drill guide hole is orientated at 90 degrees to the surface of femoral head).

Optionally, the frame also includes "R" and "L" labels adjacent to the pin holes. These labels refer to the "Right Hip" or the "Left Hip". Due to the angulation of the pin holes, the labels inform the surgeon which pin hole to use, depending on whether the surgery is being performed on the left hip or the right hip. This ensures that when the bone pins are inserted into the pin holes, the pins are directed towards rather than away from the femoral head.

The Resection Guide

The resection guide extends from the frame. The resection guide may include a first longitudinal outer edge that defines a first resection guide surface for indicating a position of a first resection plane on the femoral neck.

The resection guide may include a second longitudinal outer edge that defines a second resection guide surface for indicating a position of a second resection plane on the femoral neck.

The first resection guide surface may be located proximal of the second resection guide surface, such that the first resection guide surface represents a resection plane that corresponds to a standard offset neck resection plane, and the second resection guide surface represents a resection plane that corresponds to a high offset neck resection plane.

In some constructions of the resection guide, the first and second resection guide surfaces are parallel.

The resection guide may include a first resection guide slot and second resection guide slot. The first and/or the second resection guide slot may be configured as a cutting slot, dimensioned for receipt of a blade of a cutting tool.

The first resection guide slot may be located proximal to the second resection guide surface, such that the first resection guide slot represents a resection plane that corresponds to a standard offset neck resection plane, and the second resection guide slot represents a resection plane that corresponds to a high offset neck resection plane.

The first and second resection guide slots may be substantially parallel.

The resection guide slot may be colour coded to help the surgeon to visually distinguish which slot indicates a standard offset neck resection plane, and which slot indicates a high offset neck resection plane. For example, the peripheral edges of the slots may be provided with a colour. A slot having green peripheral edges may be used to visually indicate the slot to be used for a standard offset neck resection plane. A slot having red peripheral internal edges may be used to visually indicate the slot to be used for a high offset neck resection plane.

The Arm

The markings on the arm that enable a surgeon to visualise the true femoral neck offset may be in the form of a scale (e.g., graduated lines). For example, the scale may be graduated in 1 mm increments. The scale may start at, for example 30 mm and end at 60 mm. This is a non-limiting example.

The markings may be associated with a colour coding which allows the surgeon to visually identify whether the measured femoral neck offset is a standard offset and/or a high offset.

A first series of markings on the arm that represent a femoral head offset within a first range (e.g., between 30 mm and 40 mm) may be associated with a first colour (e.g., green). The markings may be provided in the first colour (e.g., coloured ink), or may be provided on a background of the first colour. If the connector's pointer indicates that the measured femoral head offset is within this first range, the surgeon will use the standard offset resection guide surface/slot.

A second series of markings on the arm that represent a femoral head offset within a second range (e.g., between 41 mm and 46 mm) may be associated with a second colour (e.g., amber). The markings may be provided in the second colour (e.g., coloured ink), or may be provided on a background of the second colour. If the connector's pointer indicates that the measured femoral head offset is within this second range, the surgeon will need to know the planned stem size in order to decide whether to use the standard offset resection guide surface/slot or the high offset resection guide surface/slot.

A third series of markings on the arm that represent a femoral head offset within a third range (e.g., between 47 mm to 60 mm) may be associated with a third colour (e.g., red). The markings may be provided in the third colour (e.g., coloured ink), or may be provided on background of the third colour. If the connector's pointer indicates that the measured femoral head offset is within this third range, the surgeon will use the high offset resection guide surface/slot.

The markings may be provided on opposing surface of the arm. This enables the arm to be used on either a right or a left femoral head.

The Connector

The connector has a proximal end and a distal end, and a longitudinal axis extending therebetween. When the connector is mounted onto an intramedullary rod, the longitudinal axis of the connector is substantially parallel with the femoral shaft axis.

In some constructions, the connector may be configured to ride up and down the intramedullary rod. This can be used to ensure that the frame is at the correct height to locate femoral head centre.

The arm may be retained in the slot of the connector via a friction-fit. Optionally, the connector further comprises a locking mechanism for locking the connector at a location along the length of the arm. This locking mechanism make take the form of a locking screw.

In order that the markings on the arm are visible to the surgeon when the arm is assembled with the connector, the connector may include a viewing window through which at least a portion of the markings are visible.

In some constructions, the pointer may be in the form of a line that extends in a proximal direction and/or a distal direction from the viewing window.

Optionally, the pointer may be defined as a pointed projection.

The connector may further include a resection slot or resection guide for indicating a position of a vertical resection plane on the femoral neck. In some constructions, the connector has an inferior surface and the resection guide extends in a superior direction from the inferior surface. This guides a surgeon for the placement of a vertical femoral neck cut.

The resection guide may be a cutting slot for receiving a blade of a cutting device during resection of the neck.

According to a second aspect of the invention there is provided a method for performing a controlled resection of the neck of a femur during a hip replacement procedure using a surgical apparatus comprising:

a body portion comprising:

a frame comprising an aperture, wherein the aperture is dimensioned for receiving a femoral head of the femur to position the body portion with respect to a centre of the femoral head;

a resection guide for indicating a position of a resection plane on the femoral neck, and an arm extending from the frame and including markings for reading off a femoral head offset, a connector for mounting the body portion on an intramedullary rod located in an intramedullary canal of the femur, wherein the arm is slideably adjustable relative to the connector, and wherein the connector includes a pointer, the femoral head offset being indicated by reading the position of the pointer relative to the markings on the arm, mounting the connector on the intramedullary rod;

assembling the connector with the arm;

mounting the frame on the femoral head by slidably adjusting the arm relative to the connector;

measuring the femoral head offset by determining the location of the pointer with respect to the markings on the arm, and using the resection guide to either:

mark the position of the resection plane on the neck of the femur; or guide a blade of a cutting device to resect the neck of the femur.

The frame may be removably mounted on a posterior aspect of the femoral head. Alternatively, the frame may be removably mounted on an anterior aspect of the femoral head.

The connector may include a slot configured for slidable receipt of the arm, and the step of assembling the connector with the arm includes the step of slidably inserting the arm into the slot.

The frame may include a pin hole configured for removable receipt of a bone pin for removably mounting the frame on the femoral head, and wherein the step of mounting the frame on the femoral head includes the step of inserting a bone pin through the pin hole.

BRIEF DESCRIPTION OF THE DRAWINGS

Constructions of the present invention will be described hereinafter, by way of example only, with reference to the accompanying drawings in which like reference signs relate to like elements and in which.

Figure 1:
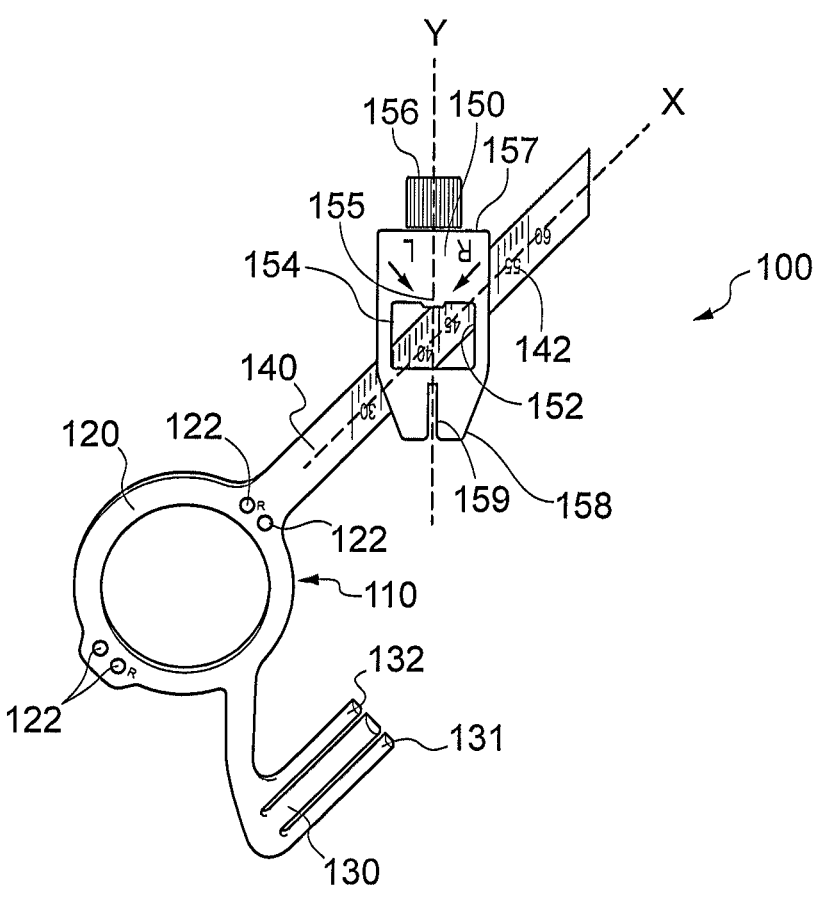
FIG. 1 illustrates a first construction of the surgical apparatus according to the invention.

The surgical apparatus 100 as shown in FIG. 1 includes a body 110. The body includes a frame 120, a resection guide 130 and an arm 140. The surgical apparatus also includes a connector 150 which is used to mount the body portion of the surgical apparatus onto an intramedullary rod. The body may be a unitary piece. This is advantageous in terms of manufacturing, and also for sterilisation of the apparatus. The body may be manufactured from metal, for example stainless steel. A non-limiting example of a suitable thickness of metal is about 6 mm.

The frame 120 is mountable on the femoral head of the femur. The frame is used to position the body portion with respect to the centre of the femoral head.

The frame includes pin holes 122, each of which is dimensioned for receipt of a bone pin for removably mounting the frame to the femoral head. The pin holes may be angled such that the drill guide hole points towards the centre of the femoral head (i.e., the drill guide hole is orientated at 90 degrees to the surface of femoral head).

The frame also includes "R" and "L" labels adjacent to the pin holes. These labels refer to the "Right Hip" or the "Left Hip". Due to the angle of the pin holes, the labels inform the surgeon which pin hole to use, depending on whether the surgery is being performed on the left hip or the right hip. This ensures that when the bone pins are inserted into the pin holes, the pins are directed towards the femoral head rather than away from it.

The resection guide 130 visually indicates to the surgeon the position of a resection plane on the femoral neck. In the construction shown, the resection guide includes two, substantially parallel, resection guide slots 131, 132. Each resection guide slot is configured to receive a blade of a cutting device during the resection of a femoral neck.

Resection guide slot 131 indicates a standard offset neck resection plane. Resection guide slot 132 indicates a high offset neck resection plane. The difference between the standard offset neck resection plane and the high offset neck resection plane will be about 7 mm. Resection of the femoral neck using the resection guide slots 131, 132 is further illustrated below with reference to FIG. 9G. The design is closed medially over the calcar and open laterally towards the trochanter. Use of either of the resection guide slots 131, 132 will result in a femoral neck resection that is 2 mm conservative of the planned neck resection. This will allow the use of a calcar reamer after preparation of the femoral canal.

The arm 140 includes markings 142 that are used to read off the femoral head offset. The markings in this construction take the form of a graduated scale. The scale shown in this construction is in 1 mm increments, starting at 30 mm (i.e., a 30 mm femoral head offset) and ending at 60 mm (i.e., a 60 mm femoral head offset). The same scale may be provided on opposing surfaces of the arm. A marking, for example "R" for right, or "L" for left, provided on the arm will indicate to the surgeon which side of the arm use.

The connector 150 is used to mount the body portion of the surgical apparatus on an intramedullary rod. In the construction shown, the connector is designed to be mounted on the intramedullary rod, but not locked onto it. The mounting may be via a friction-fit. This allows the connector to be moved up and down the intramedullary rod. Optionally, locking mechanisms may be included to lock the connector to the intramedullary rod.

The connector includes a slot 152 configured for slidable receipt of the arm 140. The slot 152 has a slot axis (X) which traverses the longitudinal axis (Y) of the connector. In the construction shown, the slot axis is angled at about 45 degrees with respect to the longitudinal axis of the connector.

The connector also includes a generally rectangular viewing window 154. The dimensions of the viewing window are such that the surgeon can view at a portion of the adjacent markings 142 on the arm 140. For example, the surgeon can view at least two adjacent markings. As shown in this first construction of the surgical apparatus, the viewing window is sufficiently large enough for the surgeon to be able to see the markings from 36 mm to 50 mm.

The connector also includes a pointer 155, shown here in the form of a line extending between the proximal end of the connector and the proximal surface of the viewing window 154. The position of the line 155 on the connector relative to the markings 142 on the arm provides the surgeon with an immediate visual readout of the femoral head offset. In the construction shown, the line 155 is aligned with the 44 mm increment of the graduated scale. Accordingly, the surgeon can see that the femoral head offset is 44 mm. Advantageously, by using the surgical apparatus of the invention the surgeon does not need to undertake any mental arithmetic, which as well as being time-consuming, may be prone to human error.

Figure 2:
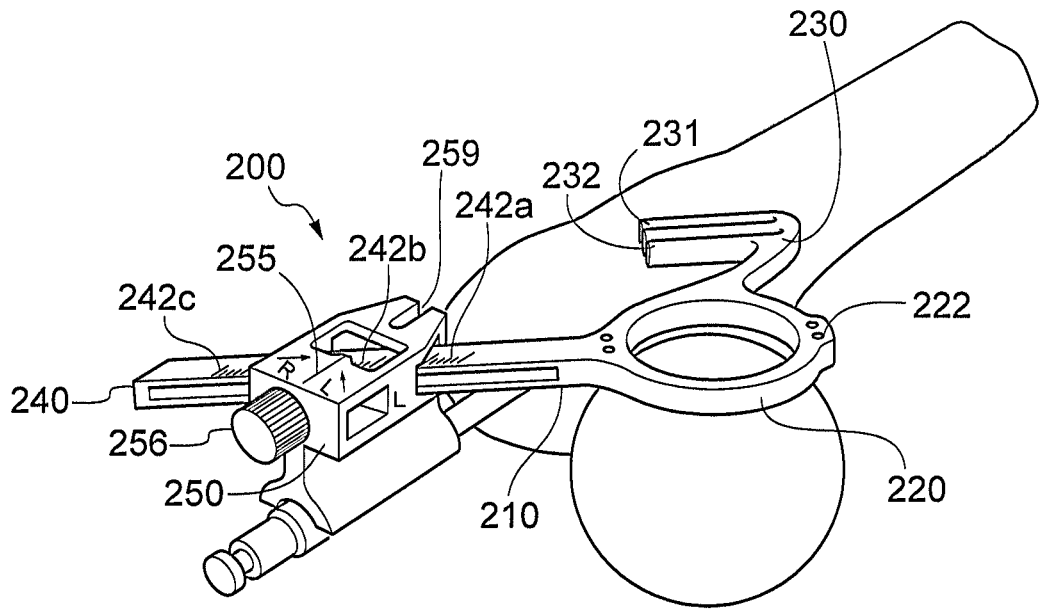
FIG. 2 illustrates a second construction of the surgical apparatus according to the invention.
Figure 3:
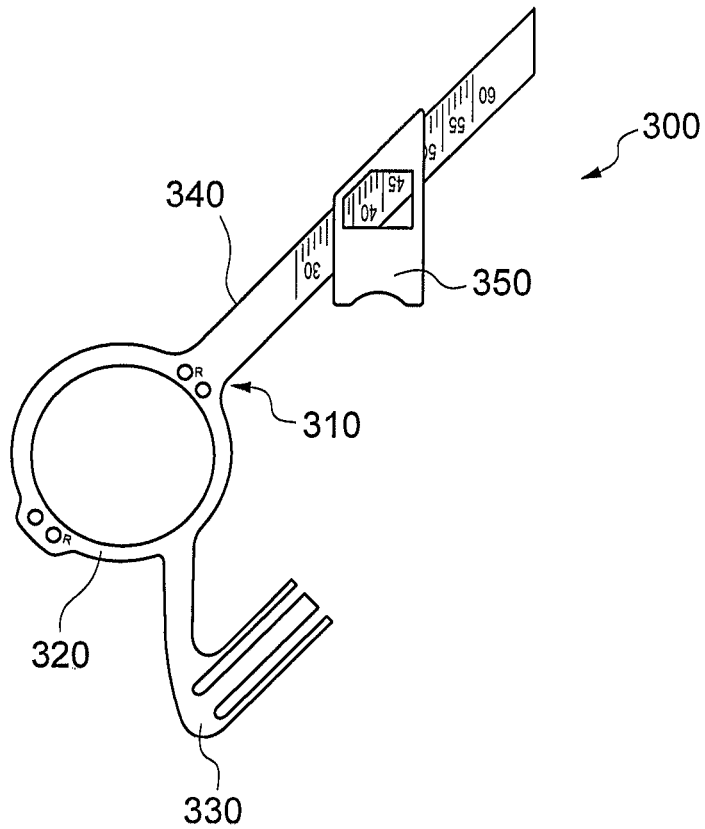
FIG. 3 illustrates a third construction of the surgical apparatus according to the invention.
Figure 4:
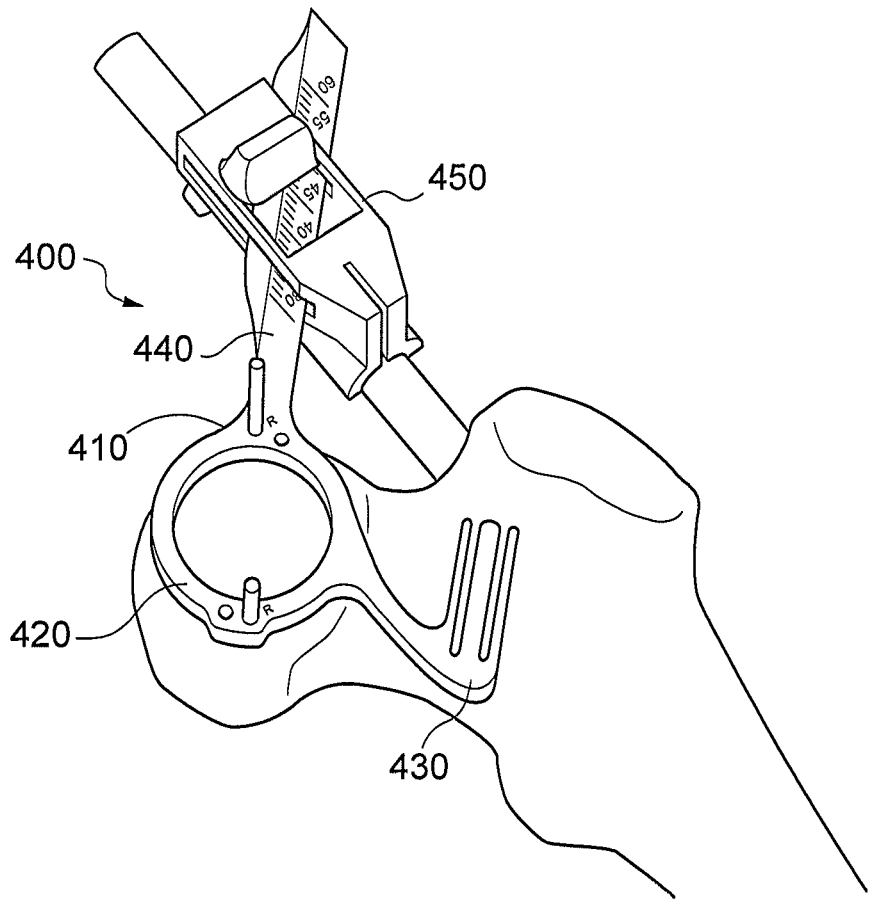
FIG. 4 illustrates a fourth construction of the surgical apparatus according to the invention.
Figure 5:
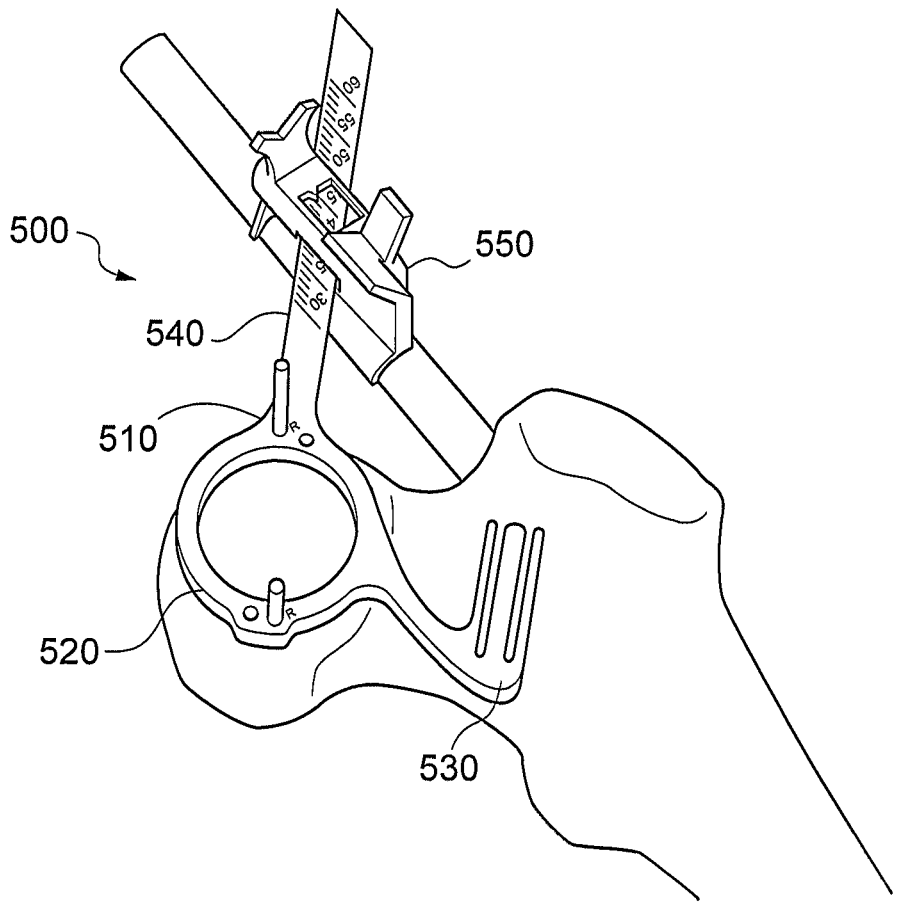
FIG. 5 illustrates a fifth construction of the surgical apparatus according to the invention.
Figure 6:
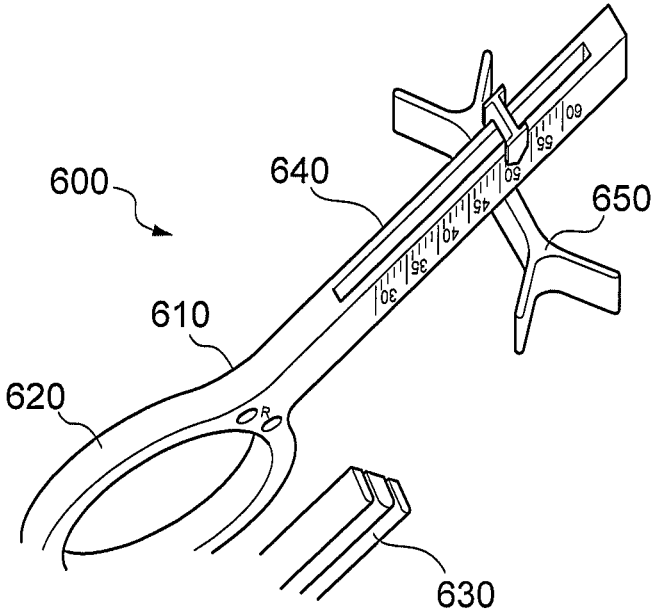
FIG. 6 illustrates a sixth construction of the surgical apparatus according to the invention.
Figure 7:
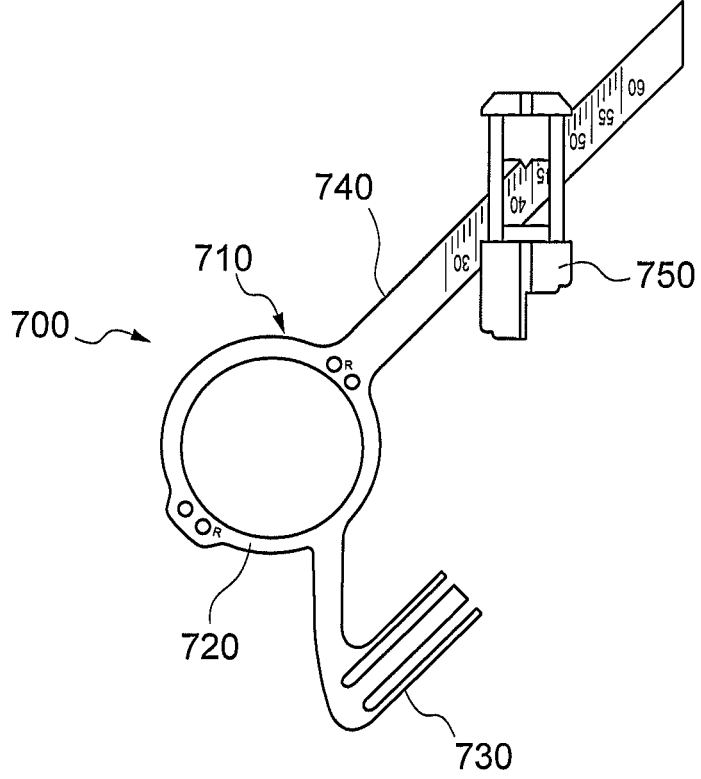
FIG. 7 illustrates a seventh construction of the surgical apparatus according to the invention.
Figure 8:
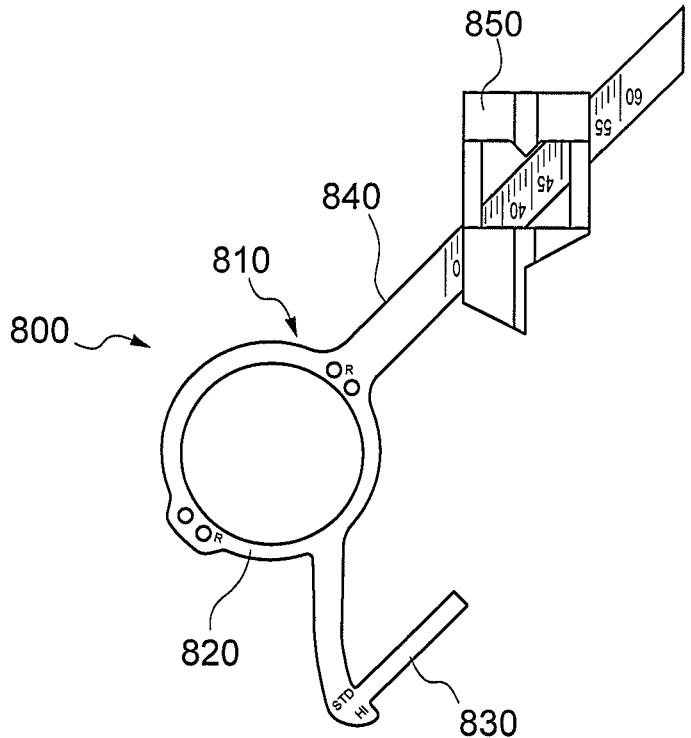
FIG. 8 illustrates an eighth construction of the surgical apparatus according to the invention.

The connector may include a "R" and a "L" label. These refer to "Right Hip" and "Left Hip". As the arm is symmetrical, the connector can be flipped over for use on either the left hip or the right hip, As shown in this construction, a locking mechanism 156 is provided on the connector, which can be used to lock the arm 140 and the connector 150 together. This prevents any inadvertent sliding movement of the arm relative to the connector, thereby ensuring an accurate reading of femoral head offset is made. In the construction shown, the locking mechanism is in the form of a locking screw provided at the proximal end 157 of the connector. This locking screw is configured for locking engagement within a groove provided on the proximal and/or distal surface of the arm. This groove is shown in FIG. 2. The groove shown this construction does not extend to the medial and lateral ends of the arm. The groove is therefore a captive groove. This ensures that whilst the arm is free to slide within the connector, until locked in place, the connector will not inadvertently fall off the end of the arm during surgery. Optionally, the groove may extend along the entire length of the arm.

Provided at the distal end 158 of the connector is a cutting slot 159. This slot may be used to perform a vertical resection of the femoral neck. This is illustrated below with reference to FIG. 9G.

A second construction of the surgical apparatus 200 is shown in FIG. 2. The construction is essentially the same as the first construction, apart from the use of colour coding to visually help the surgeon. Like parts in this construction of the surgical apparatus are referenced using the same reference numbers as in FIG. 1, incremented by 100.

The markings 242 are associated with a colour coding which allows the surgeon to visually identify whether the measured femoral neck offset is a standard neck offset and/or a high neck offset.

A first series of markings 242a provided on the arm 240 represent a femoral head offset within a first range of between 30 mm and 40 mm. The markings are black, and are provided on a green background. This is referred to as the "green range" of femoral head offset.

A second series of markings 242b provided on the arm 240 represent a femoral head offset within a second range of between 41 mm and 46 mm. The markings are black, and are provided on an amber background. This is referred to as the "amber range" of femoral head offset.

A third series of markings 242c provided on the arm 240 represent a femoral head offset within a second range of between 47 mm and 60 mm. The markings are black, and are provided on a red background. This is referred to as the "red range" of femoral head offset.

The resection guide slots 231, 232 are colour coded in a similar manner to the markings (242a, 242c). As such, the resection guide slot 232 (indicating a standard offset resection plane) is edged with green, and the resection guide slot 231 (indicating a high offset resection plane) is edged with red.

During use, if the connector's pointer 255 indicates that the measured femoral head offset is within the green range of femoral head offset, the surgeon marks the neck resection plane using the green resection guide slot 232.

During use, if the connector's pointer 255 indicates that the measured femoral head offset is within the red range of femoral head offset, the surgeon marks the neck resection plane using the red resection guide slot 231.

During use, if the connector's pointer 255 indicates that the measured femoral head offset is within the amber range of femoral head offset, the surgeon will need to know the planned stem size in order to decide whether to mark the neck resection plane using the green resection guide slot 232, or the red resection guide slot 231.

FIGS. 3 to 8 illustrate the third to eighth constructions of the surgical apparatus according to the invention. The body (310, 410, 510, 610, 710, 810) of the surgical apparatus includes a frame (320, 420, 520, 620, 720, 820), a resection guide (330, 430, 530, 630, 730 and 830), and an arm (340, 440, 540, 640, 740, 840) as discussed above with reference to FIGS. 1 and 2. Each construction of the surgical apparatus also includes a connector (350, 450, 550, 650, 750 and 850). Different designs of the connector are shown in each of the third to eighth constructions of the surgical apparatus. For example, each connector varies in the mechanism by which it is mounted to an intrameduallary rod. In addition, each connector varies in the design of the pointer.

FIG. 9 provides a non-limiting example of a flow of surgical steps in which the second construction of the surgical apparatus of the invention is used during hip arthroplasty.

Figure 9A:
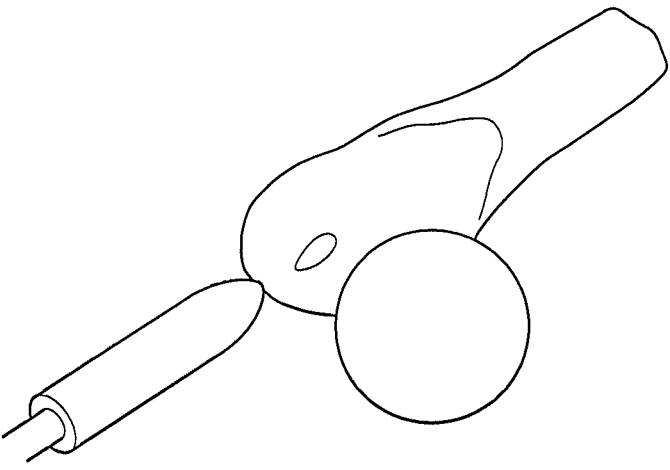
FIG. 9A-G illustrates a surgical procedure for performing a controlled resection of the neck of a femur during a hip replacement procedure.
Figure 9B:
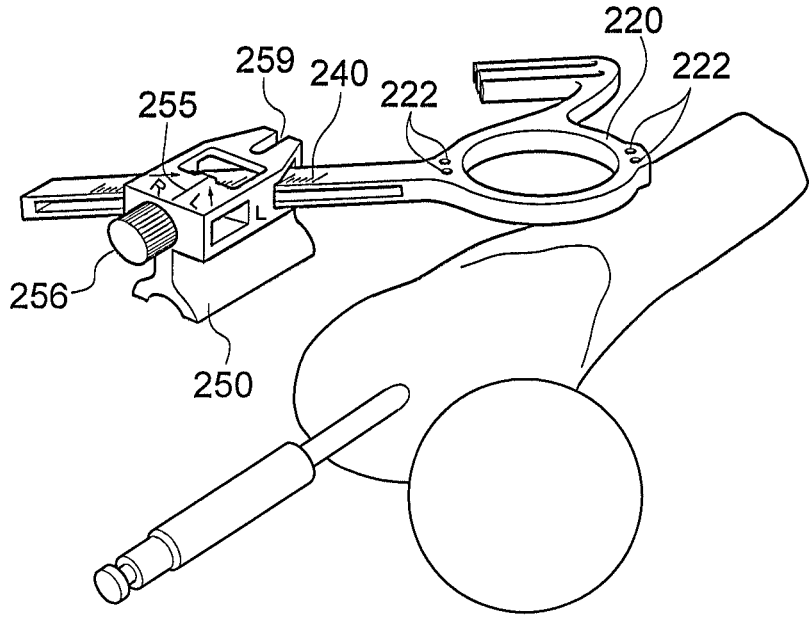

FIG. 9A: An intramedullary rod (having a fully rounded collar) is inserted into the femoral canal;

FIG. 9B: The surgical apparatus according to the invention is pre-assembled. This involves sliding the arm of the body into the slot of the connector.

Figure 9C:
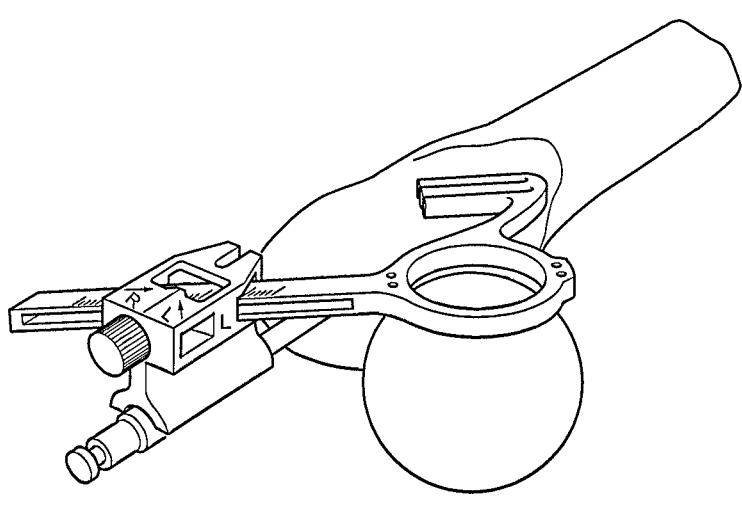

FIG. 9C: The connector 250 of the assembled surgical apparatus is then mounted onto the intramedullary rod. The surgeon the slides the arm 240, in a generally medial/lateral direction, until the frame 220 is mounted on the femoral head. The arm is then locked in position by rotating the knob of the locking screw 256 in a clockwise direction.

Figure 9D:
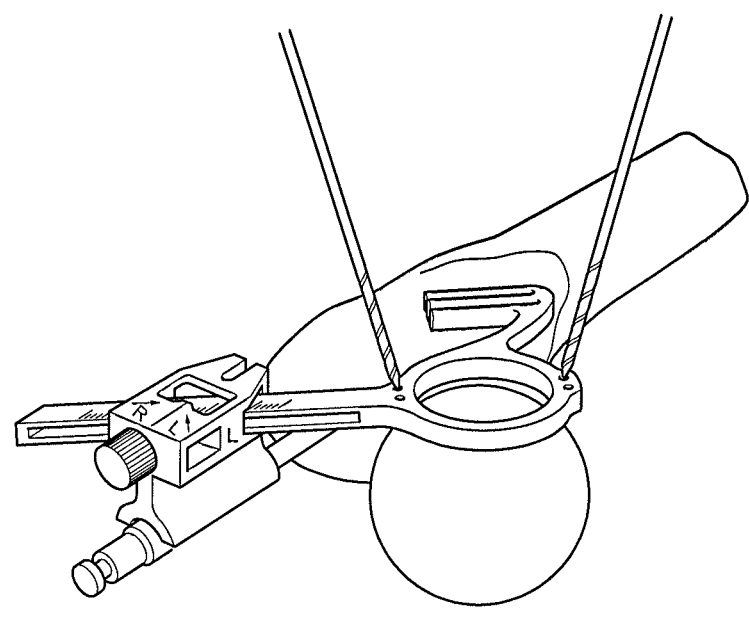

FIG. 9D: Drill holes are drilled into the femoral head using the pin holes 222 on the frame. Pins are then inserted at an angle into the femoral head to secure the frame.

Figure 9E:
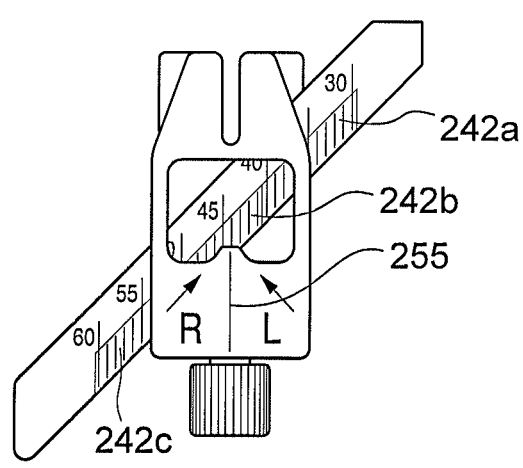

FIG. 9E: The surgeon takes a true femoral head offset measurement by looking at the relative location of the pointer 255 with the markings 242 on the arm. As shown, the pointer 255 is aligned the marking that indicated 44 mm femoral head offset. Notably, this is within "amber range" of femoral head offset.

Figure 9F:
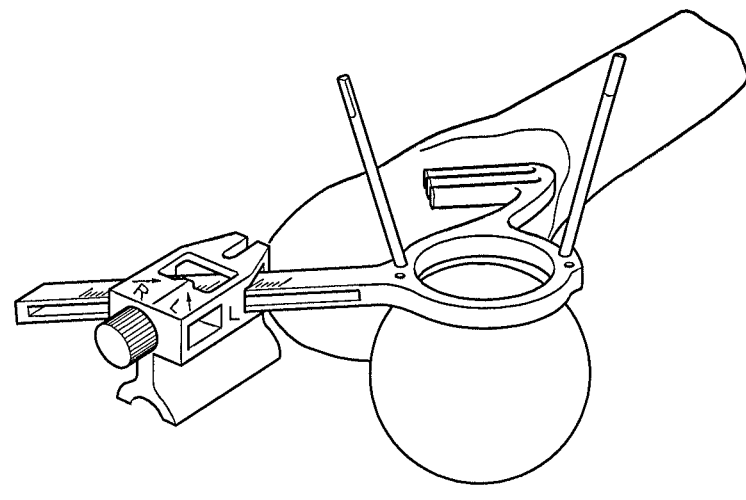

FIG. 9F: The intramedullary nail/rod is removed from the femur.

Figure 9G:
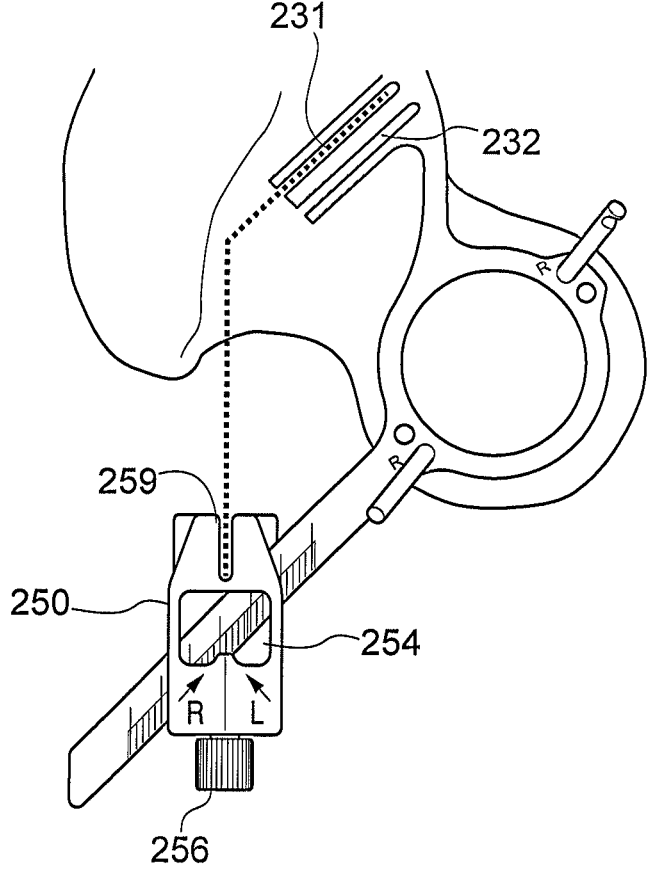

FIG. 9G: Next, the surgeon resects the femoral neck. In this schematic, the surgeon uses the cutting slot 259 on the connector 250 to make a vertical neck resection, and the red resection guide slot 231 to perform a high offset neck resection. The femoral head is then removed.

The invention claimed is:

1. A method for performing a controlled resection of the neck of a femur during a hip replacement procedure using a surgical apparatus comprising:
   a body portion comprising:
      a frame comprising an aperture, wherein the aperture is dimensioned for receiving a femoral head of the femur to position the body portion with respect to a center of the femoral head;
      a resection guide for indicating a position of a resection plane on the femoral neck, and
      an arm extending from the frame and including markings for reading off a femoral head offset,
   a connector for mounting the body portion on an intramedullary rod located in an intramedullary canal of the femur, and for slidably receiving the arm and wherein the connector includes a pointer, the femoral head offset being indicated by reading the position of the pointer relative to the markings on the arm,
   mounting the connector on the intramedullary nail;
   assembling the connector with the arm;
      mounting the frame on the femoral head by slidably adjusting the arm relative to the connector;

measuring the femoral head offset by determining the location of the pointer with respect to the markings on the arm, and
   using the resection guide to either:
      mark the position of the resection plane on the neck of the femur; or
      guide a blade of a cutting device to resect the neck of the femur.

2. The method of claim 1, wherein the method further comprises: removably mounting a frame on a posterior aspect of the femoral head.

3. The method of claim 1, wherein the method further comprises: removably mounting a frame on an anterior aspect of the femoral head.

4. The method of claim 3, wherein the connector includes a slot configured for slidable receipt of the arm, and wherein assembling the connector with the arm includes inserting the arm into said slot.

5. The method of claim 4, wherein the frame includes a pin hole configured for removable receipt of a bone pin for removably mounting the frame on the femoral head, and wherein mounting the frame on the femoral head includes inserting a bone pin through the pin hole.

6. The method of claim 2, wherein the connector includes a slot configured for slidable receipt of the arm, and wherein assembling the connector with the arm includes inserting the arm into said slot.

7. The method of claim 6, wherein the frame includes a pin hole configured for removable receipt of a bone pin for removably mounting the frame on the femoral head, and wherein mounting the frame on the femoral head includes inserting a bone pin through the pin hole.

\* \* \* \* \*